(12) United States Patent
Andino et al.

(10) Patent No.: US 9,545,625 B2
(45) Date of Patent: Jan. 17, 2017

(54) IONIC LIQUID FUNCTIONALIZED REDUCED GRAPHITE OXIDE / TIO$_2$ NANOCOMPOSITE FOR CONVERSION OF CO$_2$ TO CH$_4$

(71) Applicants: Jean Andino, Chandler, AZ (US); Tingting Gao, Tempe, AZ (US)

(72) Inventors: Jean Andino, Chandler, AZ (US); Tingting Gao, Tempe, AZ (US)

(73) Assignee: Arizona Board of Regents on Behalf of Arizona State University, Scottsdale, AZ (US)

( * ) Notice: Subject to any disclaimer, the term of this patent is extended or adjusted under 35 U.S.C. 154(b) by 443 days.

(21) Appl. No.: 14/076,764

(22) Filed: Nov. 11, 2013

(65) Prior Publication Data

US 2014/0131192 A1    May 15, 2014

Related U.S. Application Data

(60) Provisional application No. 61/724,578, filed on Nov. 9, 2012.

(51) Int. Cl.
  *C07C 31/04* (2006.01)
  *B01J 35/00* (2006.01)
  (Continued)

(52) U.S. Cl.
  CPC ............. *B01J 35/004* (2013.01); *B01J 19/123* (2013.01); *B01J 19/127* (2013.01); *B01J 21/063* (2013.01); *B01J 21/18* (2013.01); *B01J 21/20* (2013.01); *B01J 31/0284* (2013.01); *B01J 31/0295* (2013.01); *B01J 35/002* (2013.01); *B01J 35/0013* (2013.01); *B01J 37/16* (2013.01);
  (Continued)

(58) Field of Classification Search
  CPC .................... B01J 31/0277; B01J 2219/00047; B01J 35/004; B01J 21/063; B01J 21/1833; C07C 2521/18; C07C 31/04; C07C 31/043; C25B 3/04
  USPC ........................................................ 502/350
  See application file for complete search history.

(56) References Cited

U.S. PATENT DOCUMENTS

| 8,257,867 B2 * | 9/2012 | Liu | ........................ B82Y 30/00 29/592 |
| 8,450,014 B2 * | 5/2013 | Liu | ........................ B82Y 30/00 29/592 |

(Continued)

FOREIGN PATENT DOCUMENTS

| CN | 103007913 A | * | 4/2013 | |
| WO | 2005/095279 | * | 10/2005 | ............. B01D 11/04 |

OTHER PUBLICATIONS

"Enhanced photoelectrocatalytic activity of reduced graphene oxide/TiO2 composite films for dye degradation," Dongting Wang et al. Chemical Engineering Journal 198-199 (2012), pp. 547-554.*

(Continued)

*Primary Examiner* — Patricia L Hailey
(74) *Attorney, Agent, or Firm* — Quarles & Brady LLP

(57) ABSTRACT

An ionic liquid functionalized reduced graphite oxide (IL-RGO)/TiO$_2$ nanocomposite was synthesized and used to reduce CO$_2$ to a hydrocarbon in the presence of H$_2$O vapor.

18 Claims, 10 Drawing Sheets

(51) Int. Cl.

| | | |
|---|---|---|
| *B01J 19/12* | (2006.01) | |
| *B01J 21/06* | (2006.01) | |
| *B01J 21/18* | (2006.01) | |
| *B01J 31/02* | (2006.01) | |
| *B01J 37/16* | (2006.01) | |
| *B01J 21/20* | (2006.01) | |
| *C25B 3/04* | (2006.01) | |
| *C07C 1/02* | (2006.01) | |
| *B01J 38/04* | (2006.01) | |

(52) U.S. Cl.
CPC .................. *C07C 1/02* (2013.01); *C25B 3/04* (2013.01); *B01J 35/0033* (2013.01); *B01J 35/0093* (2013.01); *B01J 38/04* (2013.01); *B01J 2231/625* (2013.01); *C07C 2521/06* (2013.01); *C07C 2521/18* (2013.01); *Y02P 20/52* (2015.11); *Y02P 20/584* (2015.11)

(56) References Cited

U.S. PATENT DOCUMENTS

| | | | | |
|---|---|---|---|---|
| 8,563,169 | B2* | 10/2013 | Liu | H01M 4/13 429/209 |
| 2008/0110497 | A1* | 5/2008 | Inoue | B01J 21/063 136/256 |
| 2011/0082026 | A1* | 4/2011 | Sakatani | B01J 21/063 502/159 |
| 2012/0256138 | A1* | 10/2012 | Suh | B82Y 30/00 252/503 |
| 2012/0265122 | A1* | 10/2012 | El-Shall | B01J 37/16 204/157.47 |
| 2014/0120453 | A1* | 5/2014 | Ajayan | C01B 31/043 429/482 |
| 2014/0147377 | A1* | 5/2014 | Ho | C01B 3/042 423/658.2 |
| 2014/0275597 | A1* | 9/2014 | Zhang | C07F 7/1896 556/418 |
| 2014/0374267 | A1* | 12/2014 | Monteiro | C25D 5/10 205/104 |
| 2015/0175426 | A1* | 6/2015 | Jin | C01B 31/0469 423/448 |
| 2015/0287543 | A1* | 10/2015 | Aksay | B82Y 30/00 361/502 |

OTHER PUBLICATIONS

"Nanocomposites of TiO2 and Reduced Graphene Oxide as Efficient Photocatalysts for Hydrogen Evolution," Wenqing Fan, et al. The Journal of Physical Chemistry C 2011, 115, pp. 10694-10701.*
"Immobilized TiO2-reduced graphene oxide nanocomposites on optical fibers as high performance photocatalysts for degradation of pharmaceuticals," Lu Lin et al. Chemical Engineering Journal xxx (2016), pp. 1-10.*
"Controlled growth of TiO2 and TiO2-RGO composite nanoparticles in ionic liquids for enhanced photocatalytic H2 generation," Ganganagappa Nagaraju et al. Journal of Molecular Catalysis A: Chemical 378 (2013), pp. 213-220.*
"TiO2-RGO hybrid nanomaterials for enhanced water splitting reaction," G. Nagaraju et al. International Journal of Hydrogen Energy 40 (2015), pp. 12209-12216.*
Roy S.C. et al., "Toward Solar Fuels: Photocatalytic Conversion of Carbon Dioxide to Hydrocarbons", ACS Nano, vol. 4, Issue 3, pp. 1259-1278 (2010).
Osterloh F.E. et al.,"Inorganic Materials as Catalysts for Photochemical Splitting of Water", Chemistry of Materials, vol. 20, Issue 1, pp. 35-54 (2008).
Ni M. et al., "A Review and Recent Developments in Photocatalytic Water-Splitting Using TiO2 for Hydrogen Production", Renewable & Sustainable Energy Reviews, vol. 11, Issue 3, pp. 401-425 (2007).

Hashimoto K. et al., "TiO2 Photocatalysis: A Historical Overview and Future Prospects", Japanese Journal of Applied Physics, vol. 44, Issue 12, pp. 8269-8285 (2005).
Yao Y. et al., "Photoreactive TiO 2 /Carbon Nanotube Composites: Synthesis and Reactivity", Environmental Science & Technology, vol. 42, Issue 13, pp. 4952-4957 (2008).
Zhang H. et al., "P25—Graphene Composite as a High Performance Photocatalyst", ACS Nano, vol. 4, Issue 1, pp. 380-386 (2010).
Woan K. et al., "Photocatalytic Carbon-Nanotube—TiO2 Composites", Advanced Materials, vol. 21, Issue 21, pp. 2233-2239 (2009).
Ng Y.H. et al., "To What Extent Do Graphene Scaffolds Improve the Photovoltaic and Photocatalytic Response of TiO2 Nanostructured Films?", the Journal of Physical Chemistry Letters, vol. 1, Issue 15, pp. 2222-2227 (2010).
Leary R. et al., "Carbonaceous Nanomaterials for the Enhancement of TiO2 Photocatalysis", Carbon, vol. 49, Issue 3, pp. 741-772 (2011).
Yang N. et al., "Two-Dimensional Graphene Bridges Enhanced Photoinduced Charge Transport in Dye-Sensitized Solar Cells", ACS Nano, vol. 4, Issue 2, pp. 887-894 (2010).
Ishigami M. et al., "Atomic Structure of Graphene on SiO2", Nano Letters, vol. 7, Issue 6, pp. 1643-1648 (2007).
Wang W. et al., "Visible Light Photodegradation of Phenol on MWNT-TiO2 Composite Catalysts Prepared by a Modified Sol—Gel Method", Journal of Molecular Catalysis a: Chemical, vol. 235, Issue 1-2, pp. 194-199 (2005).
Lin J. et al.,"Photoelectric Catalytic Degradation of Methylene Blue by C60-Modified TiO2 Nanotube Array", Applied Catalysis B: Environmental, vol. 89, Issue 3-4, pp. 425-431 (2009).
Kamat P.V. et al., "Meeting the Clean Energy Demand: Nanostructure Architectures for Solar Energy Conversion", Journal of Physical Chemistry C, vol. 111, Issue 7, pp. 2834-2860 (2007).
Mohapatra S.K. et al., "Design of a Highly Efficient Photoelectrolytic Cell for Hydrogen Generation by Water Splitting: Application of Ti02-xCx Nanotubes as a Photoanode and Pt/TiO2 Nanotubes as a Cathode", Journal of Physical Chemistry C, vol. 111, Issue 24, pp. 8677-8685 (2007).
Murphy a.B., "Does Carbon Doping of TiO2 Allow Water Splitting in Visible Light? Comments on 'Nanotube Enhanced Photoresponse of Carbon Modified (CM)-n-TiO2 for Efficient Water Splitting'", Solar Energy Materials and Solar Cells, vol. 92, Issue 3, pp. 363-367 (2008).
Park J.H. et al., "Novel Carbon-Doped TiO2 Nanotube Arrays with High Aspect Ratios for Efficient Solar Water Splitting", Nano Letters, vol. 6, Issue 1, pp. 24-28 (2006).
Xu C. et al., "Nanotube Enhanced Photoresponse of Carbon Modified (CM)-n-TiO2 for Efficient Water Splitting", Solar Energy Materials and Solar Cells, vol. 91, Issue 10, pp. 938-943 (2007).
Yamashita H. et al., "Selective Formation of CH3OH in the Photocatalytic Reduction of CO2 with H2O on Titanium Oxides Highly Dispersed Within Zeolites and Mesoporous Molecular Sieves", Catalysis Today, vol. 45, Issue 1-4, pp. 221-227 (1998).
Yamashita H. et al., "Photocatalytic Synthesis of CH4 and CH3OH from CO2 and H2O on Highly Dispersed Active Titanium Oxide Catalysts", Energy Conversion and Management, vol. 36, Issue 6-9, pp. 617-620 (1995).
Anpo M. et al., "Photocatalytic Reduction of CO2 with H2O on Various Titanium Oxide Catalysts", Journal of Electroanalytical Chemistry, vol. 396, Issue 1-2, pp. 21-26 (1995).
Anpo M. et al., "Photocatalytic Reduction of CO2 with H2O on Ti-MCM-41 and Ti-MCM-48 Mesoporous Zeolite Catalysts", Catalysis Today, vol. 44, Issue 1-4, pp. 327-332 (1998).
Ikeue K. et al., "Characterization of Self-Standing Ti-Containing Porous Silica Thin Films and Their Reactivity for the Photocatalytic Reduction of CO2 with H2O", Catalysis Today, vol. 74, Issue 3-4, pp. 241-248 (2002).
Wu J.C.S. et al., "Photo Reduction of CO2 to Methanol Using Optical-Fiber Photoreactor", Applied Catalysis A: General, vol. 296, Issue 2, pp. 194-200 (2005).
Nguyen T.V., "Photoreduction of CO2 in an Optical-Fiber Photoreactor: Effects of Metals Addition and Catalyst Carrier", Applied Catalysis A: General, vol. 335, Issue 1, pp. 112-120 (2008).

(56) References Cited

OTHER PUBLICATIONS

Vijayan B. et al., "Effect of Calcination Temperature on the Photocatalytic Reduction and Oxidation Processes of Hydrothermally Synthesized Titania Nanotubes", Journal of Physical Chemistry C, vol. 114, Issue 30, pp. 12994-13002 (2010).
Ramdin M. et al., "State-of-the-Art of $CO_2$ Capture with Ionic Liquids", Industrial & Engineering Chemistry Research, vol. 51, Issue 24, pp. 8149-8177 (2012).
Gao T. et al., "Computational and Experimental Study of the Interactions Between Ionic Liquids and Volatile Organic Compounds", Physical Chemistry Chemical Physics, vol. 12, Issue 33, pp. 9830-9838 (2010).
Shen J. et al., "Ionic Liquid-Assisted One-Step Hydrothermal Synthesis of $TiO_2$-Reduced Graphene Oxide Composites", Nano Research, vol. 4, Issue 8, pp. 795-806 (2011).
Dai B. et al., "High-Quality Single-Layer Graphene Via Reparative Reduction of Graphene Oxide", Nano Research, vol. 4, Issue 5, pp. 434-439 (2011).
Koci K. et al., "Effect of $TiO_2$ Particle Size on the Photocatalytic Reduction of $CO_2$", Applied Catalysis B: Environmental, vol. 89, Issue 3-4, pp. 494-502 (2009).
Li Y. et al., "Photocatalytic Reduction of $CO_2$ with $H_2O$ on Mesoporous Silica Supported $Cu/TiO_2$ Catalysts", Applied Catalysis B: Environmental, vol. 100, Issue 1-2, pp. 386-392 (2010).
Zhang Q. et al., "Copper and Iodine Co-Modified $TiO_2$ Nanoparticles for Improved Activity of $CO_2$ Photoreduction with Water Vapor", Applied Catalysis B: Environmental, vol. 123-124, pp. 257-264 (2012).
Gao T. et al., "Ionic Liquid Functionalized Reduced Graphite Oxide / $TiO_2$ Nanocomposite for Conversion of $CO_2$ to $CH_4$", Annual Conference of the Air and Waste Management Association, AWMA 2012, Jun. 2012.
Liu L. et al., "Photocatalytic $CO_2$ Reduction with $H_2O$ on $TiO_2$ Nanocrystals: Comparison of Anatase, Rutile, and Brookite Polymorphs and Exploration of Surface Chemistry", ACS Catalysis, vol. 2, pp. 1817-1828 (2012).
Hummers, et al., Preparation of Graphitic Oxide, J. Am. Chem. Soc., 1958, 80(6):1339.
Hurum, et al., Explaining the Enhanced Photocatalytic Activity of Degussa P25 Mixed-Phase $TiO_2$ Using Epr, J. Phys. Chem. B, 2003, 107(19):4545-4549.
Hurum, et al., Recombination Pathways in the Degussa P25 Formulation of $TiO_2$: Surface Versus Lattice Mechanisms, J. Phys. Chem. B., 2005, 109(2):977-980.
Hurum, et al., Probing Reaction Mechanisms in Mixed Phase $TiO_2$ by EPR, Journal of Electron Spectroscopy and Related Phenomena, 2006, 150(2-3):155-163.
Kovtyukhova, et al., Layer-by-Layer Assembly of Ultrathin Composite Films from Micron-Sized Graphite Oxide Sheets and Polycations, Chem. Mater., 1999, 11:771-778.
Liang, et al., Minimizing Graphene Defects Enhances Titania Nanocomposite-Based Photocatalytic Reduction of $CO_2$ for Improved Solar Fuel Production, Nano Letters, 2011, 11(7):2865-2870.
Tan, et al., Photocatalytic Reduction of Carbon Dioxide into Gaseous Hydrocarbon Using $TiO_2$ Pellets, Catalysis Today, 2006, 115(1-4):269-273.
Xia, et al., Preparation of Multi-Walled Carbon Nanotube Supported $TiO_2$ and Its Photocatalytic Activity in the Reduction of $CO_2$ with $H_2O$, Carbon, 2007, 45(4):717-721.
Yang, et al., Covalent Functionalization of Polydisperse Chemically-Converted Graphene Sheets with Amine-Terminated Ionic Liquid, Chem. Commun., 2009, (26):3880-3882.
Zhang, et al., Design and Synthesis of Multifunctional Materials Based on an Ionic-Liquid Backbone, Angew. Chem. Int. Ed., 2006, 45:5867-5870.

* cited by examiner

IONIC LIQUID FUNCTIONALIZED REDUCED GRAPHITE OXIDE / TIO$_2$ NANOCOMPOSITE FOR CONVERSION OF CO$_2$ TO CH$_4$

CROSS-REFERENCE TO RELATED APPLICATIONS

This application claims the priority benefit of U.S. provisional patent application No. 61/724,578 entitled "Ionic Liquid Functionalized Reduced Graphite Oxide/TiO$_2$ Nanocomposite for Conversion of CO$_2$ to CH$_4$" filed on Nov. 9, 2012, the contents of which are incorporated by reference as if set forth in its entirety herein for all purposes.

STATEMENT REGARDING FEDERALLY SPONSORED RESEARCH

The invention was made with government support under 1253443 awarded by the National Science Foundation. The United States government has certain rights in the invention.

FIELD OF THE INVENTION

The invention relates to a photocatalytic nanocomposite, a related method of making the photocatalytic nanocomposite, and a method of using the photocatalytic nanocomposite to covert carbon dioxide into methane.

BACKGROUND OF THE INVENTION

Photocatalytic materials are drawing significant attention because of their potential for solving environmental and energy problems. Among these problems are finding ways to address the contributions of CO$_2$ to global warming while still permitting increased energy consumption, as energy plays a critical role in the quality of life improvement and economic prosperity.

One potential avenue for reduction of greenhouse gases such as CO$_2$ has been CO$_2$ photoreduction using a photocatalyst in which CO$_2$ is reduced to various less harmful products over the photocatalyst that is activated by UV radiation. To date, titanium dioxide (TiO$_2$) is one of the most studied photocatalysts because it has shown the most efficient photocatalytic activity, highest stability, low cost, as well as low toxicity. In the photocatalytic reaction, electrons and holes are produced from TiO$_2$ under UV irradiation. The electrons and holes subsequently interact with reactants (including CO$_2$) to form the products.

However, CO$_2$ photoreduction has only been performed using titanium dioxide (TiO$_2$) with limited or qualified success. One of the problems in using unmodified TiO$_2$ as a photocatalyst is that electron and hole recombination leads to low photoconversion efficiency. Although various modifications to the catalytic structure have been attempted, none of the modifications have created a commercially and industrially viable structure for CO$_2$ photoreduction.

Hence, a continued need exists for a photocatalyst that improves the kinetics of a photoreduction reaction of CO$_2$.

SUMMARY OF THE INVENTION

According to one aspect of the invention, a photocatalytic nanocomposite is provided that includes a reduced graphite oxide, a photocatalytic metal oxide in nanoparticle form, wherein the photocatalytic metal oxide in nanoparticle form is dispersed in the reduced graphite oxide. The photocatalytic metal oxide may be TiO$_2$ and may be in a mixed phase form including rutile and anatase. The reduced graphite oxide may be a powder.

The photocatalytic nanocomposite may further include an ionic moiety attached to the reduced graphite oxide. The ionic moiety may comprise $R_1R_2R_3$ in which $R_1$ is NH, $R_2$ is alkylene, and $R_3$ is a cationic group. In some forms, $R_2$ may be $C_1$ to $C_5$ alkylene, and $R_3$ may be an imidazole ring protonated or substituted at a nitrogen atom. In one more specific form, $R_2$ may be propylene and $R_3$ may be an alkyl-substituted imidazole ring.

In some instances, the reduced graphite oxide may be an ionic liquid functionalized reduced graphite oxide formed by attaching a NH$_2$-terminated ionic liquid to the reduced graphite oxide.

According to another aspect of the invention, a method of making a photocatalytic nanocomposite of this type is provided. The method of making a photocatalytic nanocomposite includes oxidizing graphite to form a reduced graphite oxide and mixing the reduced graphite oxide with TiO$_2$ nanoparticles to form the photocatalytic nanocomposite. The reduced graphite oxide may be functionalized with a NH$_2$-terminated ionic liquid to form an ionic liquid functionalized reduced graphite oxide before the step of mixing. The NH$_2$-terminated ionic liquid may an imidazole such as, for example, a 1-butyl-3-methylimidazolium-based ionic liquid (e.g., 1-butyl-3-methylimidazolium chloride).

According to still another aspect of this invention a method of CO$_2$ photoreduction is provided. The method of CO$_2$ photoreduction includes contacting reactants of CO$_2$ and H$_2$O over a photocatalytic nanocomposite of the type described herein and reacting the CO$_2$ and H$_2$O over the photocatalytic nanocomposite to produce products including CH$_4$. In some forms, the products may be substantially free of CO gas. In some forms, the CH$_4$ may have a production rate in excess of 10 μmol/g catalyst-hr or in excess of 250 μmol/g catalyst-hr.

According to one specific example, an ionic liquid functionalized reduced graphite oxide (IL-RGO)/TiO$_2$ nanocomposite was synthesized and used to reduce CO$_2$ to a hydrocarbon in the presence of H$_2$O vapor. IL-RGO was synthesized through chemically attaching the ionic liquid, 1-butyl-3-methylimidazolium chloride (C$_4$mimCl), to a graphite oxide (GO) surface and simultaneously reducing GO to RGO in a basic reaction environment. As a comparison, reduced graphite oxide (RGO) was synthesized using the same procedure, but without adding the ionic liquid. The SEM image revealed that IL-RGO/TiO$_2$ contained a homogeneous dispersion of graphite flakes with TiO$_2$ nanoparticles. Diffuse Reflectance Infrared Fourier Transform Spectroscopy (DRIFTS) was used to study the conversion of CO$_2$ and H$_2$O vapor over the IL-RGO/TiO$_2$ catalyst. Under UV-Vis irradiation, two new peaks were detected in the infrared spectrum after just 40 seconds of irradiation. The intensities of these peaks continuously increased in subsequent spectra that were taken under longer irradiation time. The two peaks detected as products were characteristic of CH$_4$. Background experiments that were conducted confirmed that CH$_4$ was indeed generated from the reduction of CO$_2$ over the IL-RGO/TiO$_2$ catalyst surface. A CH$_4$ production rate of 279 μmol/g catalyst-hr (as measured using DRIFTS) over a 55 minute period was calculated. These findings suggest the direct, selective formation of CH$_4$ in the absence of CO.

These and still other advantages of the invention will be apparent from the detailed description and drawings. What follows is merely a description of some preferred embodiments of the present invention. To assess the full scope of the invention the claims should be looked to as these preferred embodiments are not intended to be the only embodiments within the scope of the claims.

DETAILED DESCRIPTION OF THE INVENTION

Figure 1:
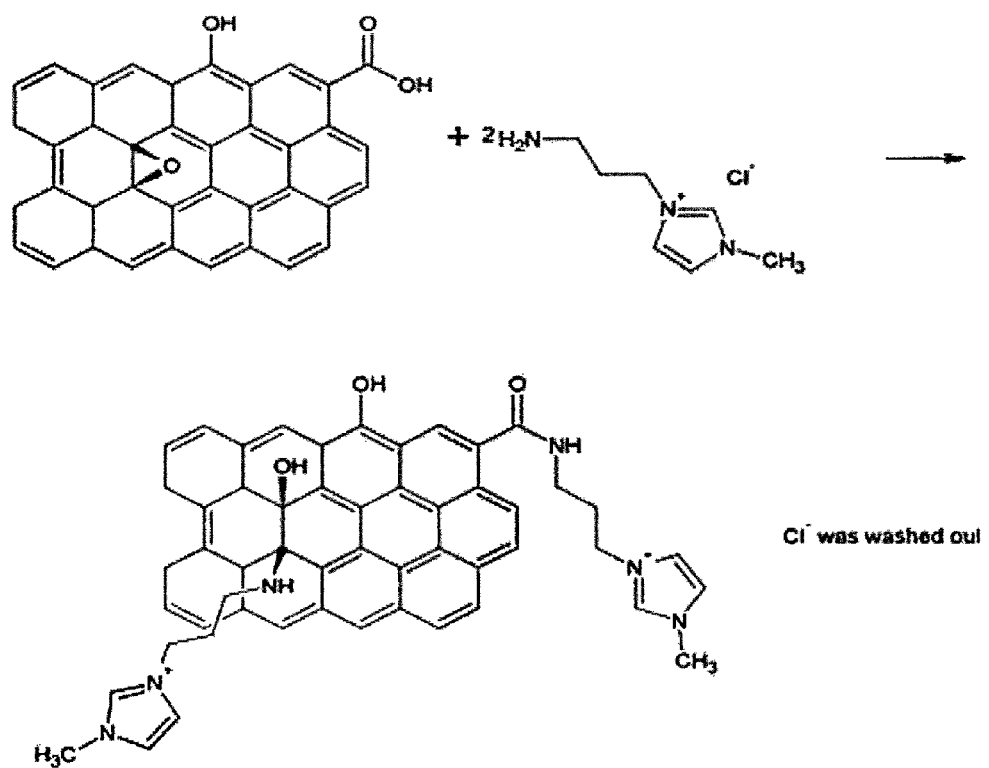
FIG. 1 shows the overall synthesis of ionic liquid functionalized reduced graphite oxide (IL-RGO).

Carbonaceous nanomaterials have unique properties and the potential to control the structural and electrical properties of photocatalysts. The presence of a carbon material such as carbon nanotubes (CNTs) or graphene might potentially reduce electron and hole recombination in the photocatalyst via transport of the electrons to the conductive carbon material. By improving the separation of the charges, recombination may be avoided thereby enhancing the photoconversion efficiency of $TiO_2$. Indeed, to date some nanocarbon (for example, CNTs or graphene)/$TiO_2$ composites have shown improved photocatalytic activity over $TiO_2$ in various applications (for example, the photooxidation of environmental pollutants).

As compared to cylindrical CNTs, planar graphene may have a smaller electron transfer barrier. As a result, the electron-hole recombination may be less. Graphene is an atomic sheet of $sp^2$-bonded carbon atoms that are arranged into a honeycomb structure. The high surface area of graphene may increase the adsorption of reactants and provide more active sites. Nearly 90% enhancement in photocurrent was seen for reduced graphene oxide described below, which serves as an electron collector and transporter in the graphene-$TiO_2$ composite. A significant enhancement in the reaction rate for the degradation of methylene blue was observed using a P25 (Degussa)-graphene composite material in contrast with a bare P25 (Degussa) or a P25 (Degussa)-CNT material with the same carbon content. In addition, a decrease in charge transfer resistance of graphene/P25 (Degussa) sample was observed versus P25 (Degussa) alone.

Presently, there are only a few examples regarding the use of $TiO_2$ nanocarbon materials for the conversion of carbon dioxide ($CO_2$) and $H_2O$ vapor to fuels. Xia et al. synthesized multi-walled carbon nanotube (MWCNT) supported $TiO_2$ and investigated its photocatalytic activity in the reduction of $CO_2$ with $H_2O$ (Xia, X. H.; Jia, Z. H.; Yu, Y.; Liang, Y.; Wang, Z.; Ma, L. L., Preparation of multi-walled carbon nanotube supported $TiO_2$ and its photocatalytic activity in the reduction of $CO_2$ with $H_2O$. *Carbon* 2007, 45, 717-721.). Sol-gel and hydrothermal methods were used to synthesize the MWCNT/$TiO_2$ composite. Both syntheses methods led to the formation of $C_2H_5OH$, HCOOH and $CH_4$. The total carbonaceous yields of the products were higher than the reported yields in the literature, which focused on using other materials to modify $TiO_2$ rather than carbon (i.e., Cu doping, Cu—Fe co-doping $TiO_2$/porous silica, $TiO_2$ nanotube). This result suggests that carbon-containing $TiO_2$ materials may be better than other materials in terms of enhancing $CO_2$ photoconversion efficiency.

It appears there has been only one instance in which an externally mixed graphene/$TiO_2$ material was applied to $CO_2$ photoreduction. Liang, Y. T.; Vijayan, B. K.; Gray, K. A.; Hersam, M. C., Minimizing Graphene Defects Enhances Titania Nanocomposite-Based Photocatalytic Reduction of $CO_2$ for Improved Solar Fuel Production. *Nano Letters* 2011, 11, 2865-2870. A solvent exfoliated graphene/P25 thin film and a thermally reduced graphite oxide/P25 thin film were used as the photocatalysts, and $CH_4$ was the major product identified. The $CH_4$ production rates of exfoliated graphene/P25 thin film and a thermally reduced graphite oxide/P25 thin film were 8.1 $\mu mol/m^2$-hr and 1.8 $\mu mol/m^2$-hr, respectively. The results indicate that $TiO_2$/graphene may be selective towards $CH_4$ production but provided low reaction rates.

In this disclosure, a novel synthesis method was used to create an improved graphene type carbon/$TiO_2$ composite material for $CO_2$ photoreduction, and the product of the $CO_2$ photocatalytic reaction in the presence of water vapor was studied. Instead of adding $TiO_2$ and the graphene type material separately, a nanocomposite material was formed. Graphene is a single atomic layer of $sp^2$ carbon structure. In the disclosed method and resulting structure, carbon layers were separated by oxidizing natural graphite to form graphite oxide and subsequently functionalizing graphite oxide with a $NH_2$-terminated ionic liquid. At the same time graphite oxide was reacted to form reduced graphite oxide (RGO) in a basic reaction environment. The high solubility of the ionic liquid in water makes it possible for an ionic liquid functionalized reduced graphite oxide (IL-RGO) to mix well with $TiO_2$ nanoparticles in water. Moreover, the ionic liquid, which is functionalized to the RGO surface, may introduce surface charge to the RGO. The charge repulsion may help to further separate the graphite layers. The high surface area of the layer-separated graphite material may enhance the adsorption of the reactants, i.e. $CO_2$ and $H_2O$ vapor, thus creating more reactive sites.

In addition, $NH_2$-ionic liquid cations may significantly enhance the ability to attract $CO_2$ via amine group-$CO_2$ interactions. Therefore, the amine-functionalized ionic liquid may also enhance the adsorption of $CO_2$. Previous experimental results indicate that the $C_4mimCl$ ionic liquid does not interact with alkanes. $CH_4$ is a potential product of $CO_2$ photoreduction using $TiO_2$ or modified $TiO_2$ catalyst. Therefore, the ionic liquid may be able to selectively adsorb the reactant, $CO_2$, but quickly dissociate the potential product, $CH_4$, thus promoting the photoreduction of $CO_2$.

The IL-RGO/$TiO_2$ nanocomposite was applied to reduce $CO_2$ in the presence of $H_2O$ vapor. The products of $CO_2$ photoreduction over the IL-RGO/$TiO_2$ was compared with the product formation data that were reported in the literature using pristine $TiO_2$ (P25) and other modified $TiO_2$ in order to provide an initial examination of the selectivity towards different products.

In the examples provided below, the new method was used to synthesize a carbon/semiconductor composite material via attaching ionic liquid to graphite oxide surface to obtain the ionic liquid functionalized reduced graphite oxide (IL-RGO), and mixing it with $TiO_2$ nanoparticles in solution. The successful synthesis of this material was confirmed by Raman spectra, XRD, XPS and SEM. Comparing RGO without functionalized ionic liquid, the IL-RGO layers were separated and IL-RGO flakes can be clearly seen in the SEM images. In addition, the SEM images showed that $TiO_2$ nanoparticles are dispersed with IL-RGO flakes. The photoreduction of $CO_2$ over IL-RGO/$TiO_2$ in the presence of $H_2O$ vapor was investigated using Diffuse Reflectance Infrared Fourier Transform Spectroscopy (DRIFTS). $CH_4$ was formed after just 40 seconds of UV-Vis irradiation over the catalyst of IL-RGO/$TiO_2$. The IR features of $CH_4$ increased as the irradiation time increased. However, no product was found for the photoreduction of commercial P25 under the same experimental conditions. Therefore, the presence of IL-RGO significantly enhances the photocatalytic activity of P25 due to the enhanced electron-hole separation. In addition, $CH_4$ was found to be the only product for IL-RGO/$TiO_2$.

The regeneration and reuse of IL-RGO/$TiO_2$ catalyst for $CO_2$ photoreduction was also investigated. The regenerated catalyst can produce almost identical amount of $CH_4$ at the same irradiation times. A $CH_4$ production rate of 279 µmol/g catalyst-hr over a 55 minute period was calculated.

The following examples are presented for illustrative purposes only, and are not intended to limit the scope of the present invention in any way.

EXAMPLES

Synthesis of the 1 L-RGO/$TiO_2$ Composite

Synthesis of the ionic liquid reduced graphite oxide/$TiO_2$ (IL-RGO/$TiO_2$) composite involved three basic steps: synthesis of graphite oxide, functionalization and reduction of the graphite oxide in order to make the material more conductive, and addition of the $TiO_2$ to allow for photoactivity.

Synthesis of Graphite Oxide

Graphite Oxide (GO) was synthesized from natural graphite powder (325 mesh, Alfa Aesar) by the method of Hummers and Offeman (Hummers, W. S.; Offeman, R. E., Preparation of Graphitic Oxide. Journal of the American Chemical Society 1958, 80, 1339-1339). Prior to synthesis using Hummers and Offeman's method, the graphite powder was pre-oxidized. Otherwise, incompletely oxidized graphene-core/GO-shell particles were observed in the final product. The pre-oxidation procedure followed the method of Kovtyukhova et al. (Kovtyukhova, N. I.; Ollivier, P. J.; Martin, B. R.; Mallouk, T. E.; Chizhik, S. A.; Buzaneva, E. V.; Gorchinskiy, A. D., Layer-by-layer assembly of ultrathin composite films from micron-sized graphite oxide sheets and polycations. *Chemistry of Materials* 1999, 11, 771-778.) Briefly, the pre-oxidation process used concentrated $H_2SO_4$, $K_2S_2O_8$ and $P_2O_5$ to oxidize the graphite powder. The resultant product was subsequently thermally isolated and allowed to cool to room temperature. After cooling, the product was diluted and washed with distilled water until the water's pH became neutral. The product was dried in air at ambient temperature overnight and subjected to oxidation by Hummers and Offeman's method. The pre-oxidized graphite powder was further oxidized using 0° C. concentrated $H_2SO_4$ and $KMnO_4$. The reaction was terminated by the addition of a large amount of distilled water and 30% $H_2O_2$ solution. The mixture was centrifuged with 1:10 HCl solution to remove metal ions. Also, additional distilled water washing was done to the mixture until a neutral pH was achieved. The mixture was dark brown in color. The GO was added to distilled water and sonicated for 15 minutes to separate the GO layers. Finally, the GO sample was obtained by centrifugation of the GO solution at 5000 rpm for 30 minutes.

It is observed that this oxidation step may help to prevent the graphite from aggregating during mixing, as might occur when using natural graphite flakes. This is evidenced by SEM images in the results below in which the flakes remain separated.

Ionic Liquid Functionalized Reduced Graphite Oxide (IL-RGO)

The overall reaction for the synthesis of IL-RGO is presented in FIG. 1. A $NH_2$-terminated ionic liquid of 1-butyl-3-methylimidazolium chloride ($NH_2$—$C_4$mimCl) was synthesized using a process that has been reported previously for the synthesis of $NH_2$-terminated 1-butyl-3-methylimidazolium bromide ($NH_2$—$C_4$mimBr). See e.g.: Yang, H. F.; Shan, C. S.; Li, F. H.; Han, D. X.; Zhang, Q. X.; Niu, L., Covalent functionalization of polydisperse chemically-converted graphene sheets with amine-terminated ionic liquid. *Chemical Communications* 2009, 3880-3882; and Zhang, Y. J.; Shen, Y. F.; Yuan, J. H.; Han, D. X.; Wang, Z. J.; Zhang, Q. X.; Niu, L., Design and synthesis of multifunctional materials based on an ionic-liquid backbone. *Angewandte Chemie-International Edition* 2006, 45, 5867-5870.

First, 3-chloropropylamine hydrochloride (Sigma Aldrich, 98%) and 1-methylimidazole (Sigma Aldrich, 99%) were added to ethanol (Sigma Aldrich, ≥99.5%). The mixture was then refluxed under nitrogen for 24 hours. The resulting turbid mixture was purified by re-crystallization from ethanol and ethyl acetate as anti-solvent. Finally, the resulting ionic liquid was dried under $N_2$ at 60° C. overnight.

The $C_4$mimCl functionalized RGO synthesis is based on an epoxide ring-opening reaction between GO and $NH_2$—$C_4$mimCl. $NH_2$—$C_4$mimCl was added into a GO dispersed solution. The salt effect of the GO sheet occurred due to the presence of the ionic liquid. The epoxide ring-opening reaction can be catalyzed by a base. Therefore, KOH was added into the turbid mixture solution. The solution was subjected to ultrasonication for 30 minutes. Lastly, the homogeneous solution was vigorously stirred at 80° C. for 24 hours. The resulting solution was washed using ethanol and distilled water several times until the pH was neutral. The resulting solution was subjected to the IL-RGO/$TiO_2$ nanocomposite material synthesis process. The IL-RGO solution was dried at room temperature for IL-RGO material characterization. For comparison, RGO was synthesized using the same procedure, but without adding the $NH_2$—$C_4mimCl$.

IL-RGO/TiO$_2$ Nanocomposite Synthesis $TiO_2$ nanoparticles (Evonik P25) were mixed with distilled water and 1-Butyl-3-methylimidazolium tetrafluoroborate ($C_4mimBF_4$, Sigma Aldrich, 98%) ($H_2O$:$C_4mimBF_4$=9:1 by volume) to make a $TiO_2$ suspension. Before making the IL-RGO/TiO$_2$ composite, the IL-RGO solution was ultrasonicated for 30 minutes and stirred for 1 hour. Later, the IL-RGO solution was added to the $TiO_2$ suspension and vigorously stirred for one hour. The mass percentage of IL-RGO was 3.5% of the composite material. The IL-RGO/TiO$_2$ mixture was washed until the pH became neutral. Then the mixture was ultrasonicated for 30 minutes and dried at 80° C. overnight. Eventually, the sample was ground to powder for use in the $CO_2$ conversion experiments. For comparison, the RGO/TiO$_2$ was synthesized using the same procedure.

Material Characterization

Raman spectra of GO and IL-RGO were collected using a custom built Raman spectrometer in a 180° geometry. The sample was excited using a 100 mW compass 532 nm laser. The data were collected using an Acton 300i spectrograph and a back thinned Princeton Instruments liquid nitrogen cooled CCD detector. The spectral resolution was 3.5 cm$^{-1}$. X-ray Diffraction (XRD) data were collected with a high resolution X-ray diffractometer (PANALYTICAL X'PERT PRO) using Cu-K$\alpha$ radiations and an X'celerator detector. Scanning electron microscopy (SEM) was performed using an XL30 ESEM-FEG. X-ray photoelectron spectroscopy (XPS) was performed using a VG ESCALAB 220i-XL aluminum-K$\alpha$ (1486.6 eV) X-ray source.

Figure 2:
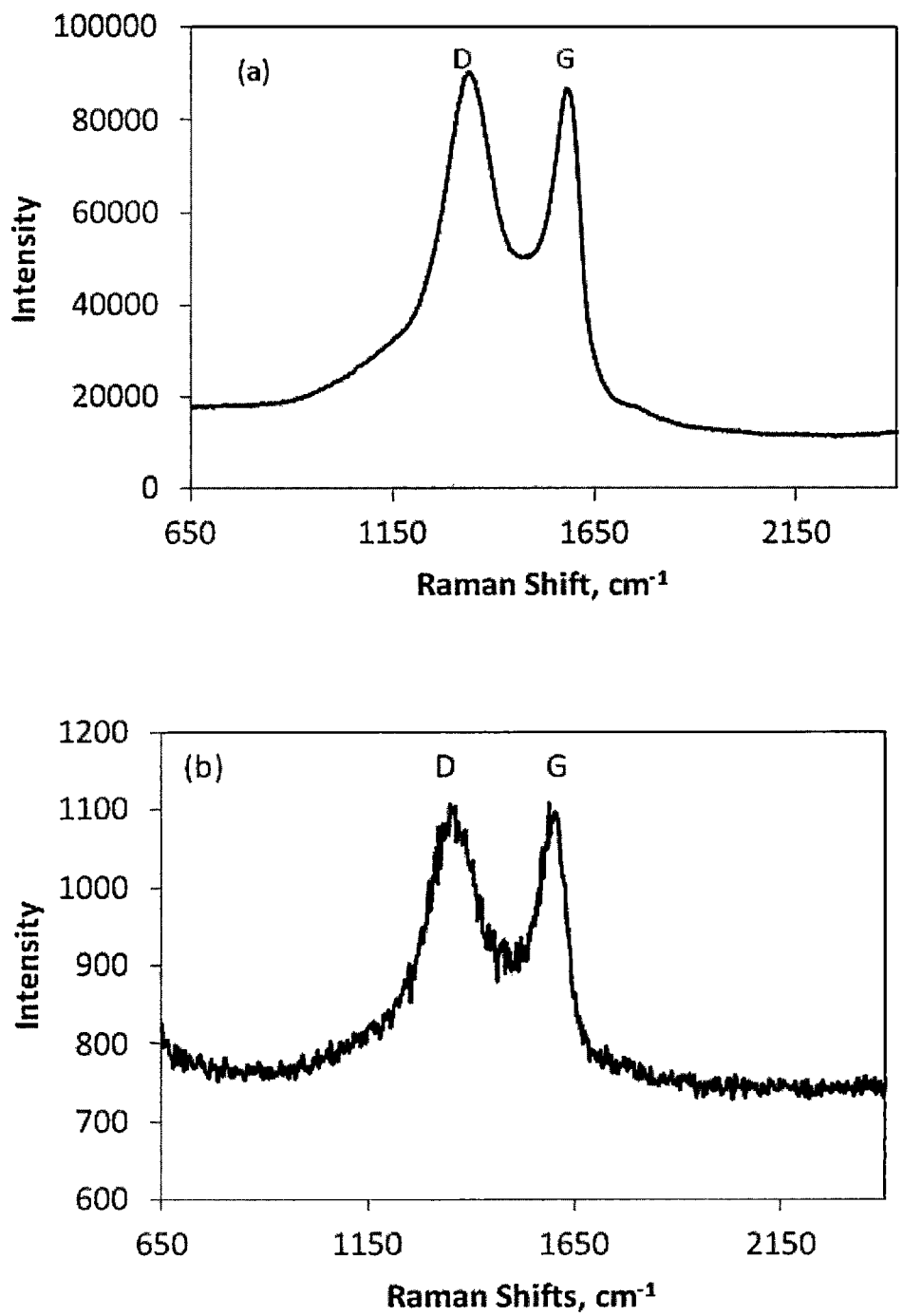
FIG. 2 shows the Raman spectra of (a) GO and (b) IL-RGO.

The Raman spectra of GO and IL-RGO are shown in FIG. 2. In the Raman spectrum of GO in FIG. 2a, the G band at 1580 cm$^{-1}$ is related to the in-plane vibration of the sp$^2$ bonded carbon atoms. The D band at 1339 cm$^{-1}$ is associated with the vibration of sp$^3$ bonded carbon atoms, which corresponds to the disordered structure of the GO. The D/G band intensity ratio of GO is 1.03. In the Raman spectrum of IL-RGO in FIG. 2b, the D/G band intensity ratio is 0.94. A decrease of the D/G band intensity ratio of IL-RGO suggests that part of the disorder structures were restored to in-plane sp$^2$ structures. The restoration of sp$^2$ carbon structure indicates an increase in the conductivity of the material. Thus, IL-RGO is likely to transfer the electrons produced from $TiO_2$ under UV irradiation.

Figure 3:
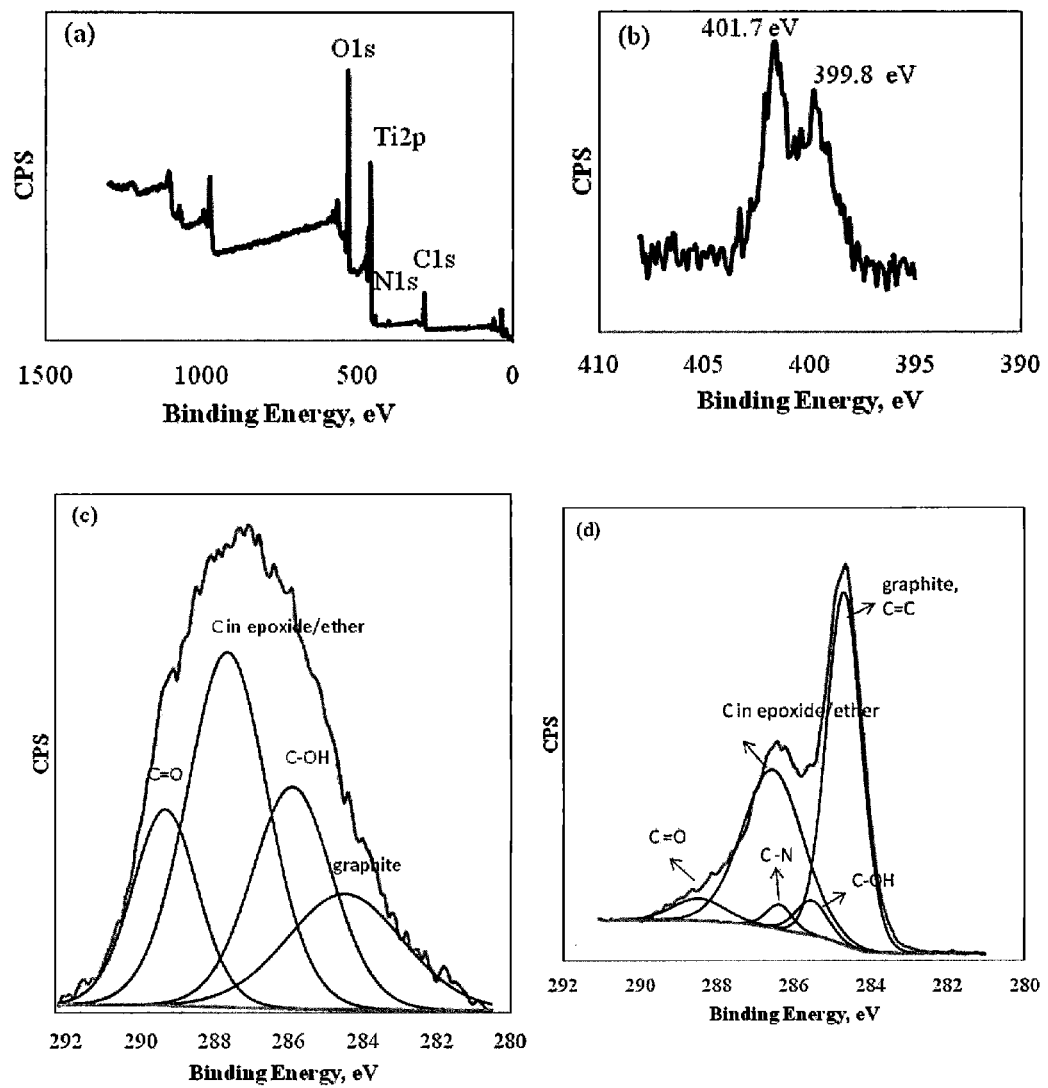
FIG. 3 shows XPS spectra for (a) wide scan survey of IL-RGO/$TiO_2$, (b) high resolution XPS spectrum of N1s, (c) high resolution XPS spectrum of C1s in GO, and (d) high resolution XPS spectrum of C1s in IL-RGO.

X-ray spectroscopy (XPS) was used to characterize the chemical composition of the material. The XPS spectra are presented in FIG. 3. The wide scan survey in FIG. 3a shows that all the expected elements, Ti, O, C and N, are present in the IL-RGO/TIO$_2$ sample. The high resolution XPS spectra of the IL-RGO/TiO$_2$ sample were examined for the presence of the anion of the functionalized ionic liquid, Cl$^-$, or the elements from the solvents used in the synthesis process. No peak associated with Cl$^-$ or any element from the solvents used in the synthesis was found. Therefore, Cl$^-$ and solvents used were completely washed out of the sample. The high resolution XPS spectrum of N1s in FIG. 3b shows that the N1s band appears at 401.7 eV, with a lower binding energy shoulder at 399.8 eV. This XPS feature of N1s is shown in both the IL-RGO/TiO$_2$ sample and the IL-RGO without adding TiO$_2$. This confirms the presence of the IL-NH$_2$ unit in IL-RGO. In addition, the small peak of C—N at 286.3 eV in the high resolution XPS spectrum of C1s in the IL-RGO sample in FIG. 3d further confirms that the $NH_2$ terminated ionic liquid was present in the sample.

The atomic concentration ratio of carbon to oxygen (C/O) determined using the XPS data of GO was 0.8, while the C/O ratio for IL-RGO determined using the XPS data was 1.4. The atomic concentration of the C—N peak shown in FIG. 3d contributes to 2.6% of the total carbon from IL-RGO. According to the molecular structure of $C_4mimCl$, the maximum percentage of carbon content that could be introduced to IL-RGO by simply attaching the ionic liquid is 6.0%. If it is assumed that the atomic concentration of oxygen does not change in the process of GO conversion to IL-RGO, the maximum C/O ratio should be 0.9. However, the actual C/O ratio of IL-RGO determined using XPS data is 1.4, suggesting that a large number of oxygen groups disappeared in the synthesis of the IL-RGO sample. Hence, GO was significantly reduced.

High resolution XPS spectra of C1s in GO and IL-RGO are shown in FIGS. 3c and 3d, respectively. Carbon has multiple binding configurations, including graphite C═C, C═O, C—OH, and C in the epoxide/ether. Comparing the peaks for different binding configurations, the atomic concentration of the graphite peak (C═C) in GO is 18.6% of carbon in all binding configurations. The maximum atomic concentration of the graphite peak contributed from the attached ionic liquid is 2.6%. However, the atomic concentration of graphite peak in IL-RGO accounts for 50.4% of that of the carbon in all binding configurations. This confirms that partial sp$^2$ graphite structures were restored. In addition, when the IL-RGO was synthesized from GO, the color of the sample changed from dark-brown to dark-gray. The change in color also strongly suggests that GO was reduced.

Figure 4:
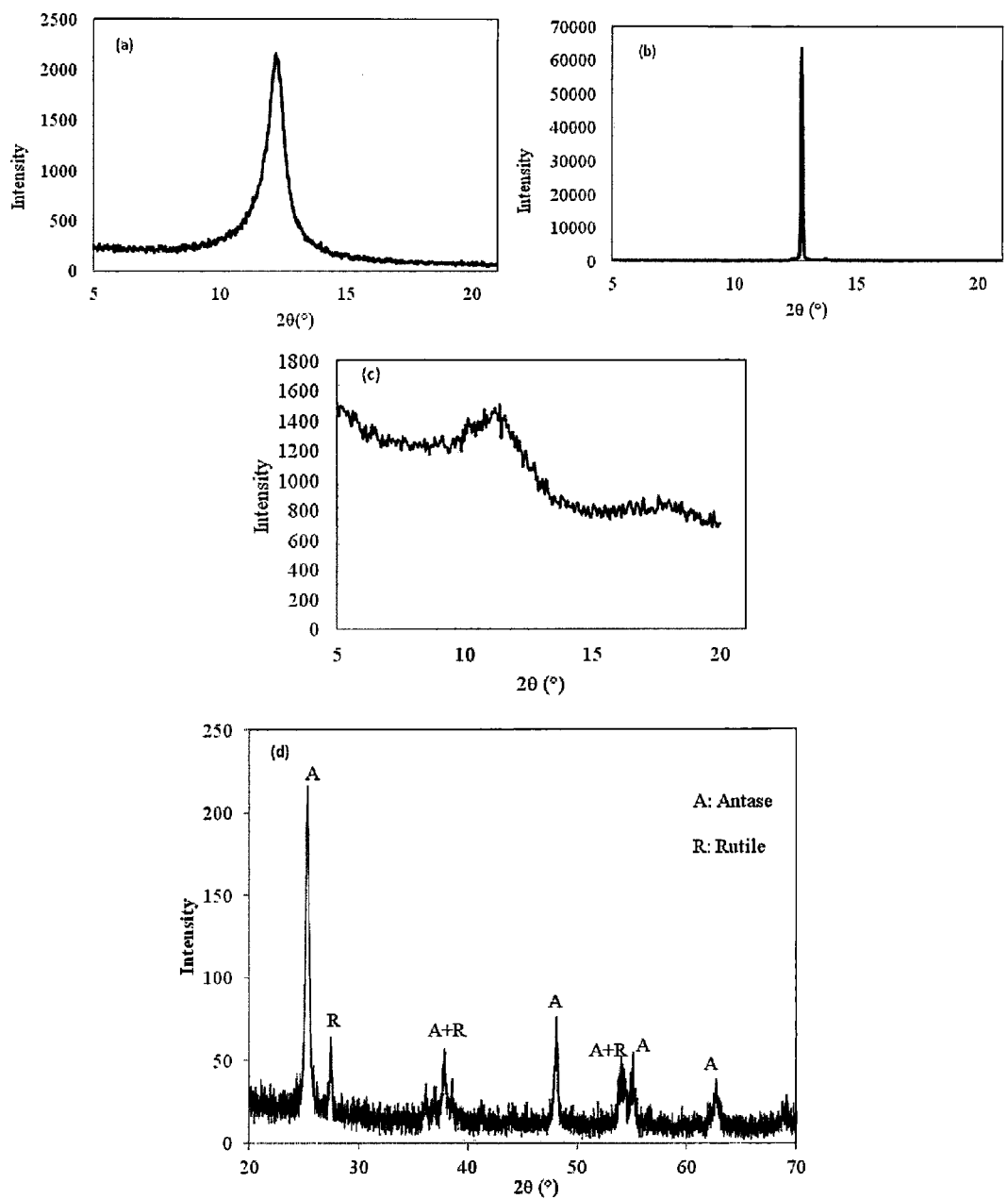
FIG. 4 shows X-ray Diffraction (XRD) peaks of (a) GO, (b) RGO, and (c) IL-RGO, and (d) XRD peaks of IL-RGO/$TiO_2$ scanning from $2\theta=20°\sim70°$.

Turning now to FIG. 4, the X-ray diffraction (XRD) data show that the diffraction peak of GO appears at 2θ=12.2° in FIG. 4a. This corresponds to an average interlayer space of 0.72 nm. The XRD peak for RGO without functionalized IL appears at 2θ=12.7° in FIG. 4b, corresponding to the average interlayer spacing of 0.70 nm, whereas IL-RGO has a weak and broad diffraction peak at 2θ=11° in FIG. 4c. As compared to GO, the slightly reduced interlayer space of RGO is likely due to the decreased number of oxygen groups. The calculated interlayer spaces of GO and RGO demonstrate that the interlayer spaces are similar within the GO structure and RGO structure. Different from the sharp XRD peaks of GO in FIG. 4a and RGO in FIG. 4b, the broad X-ray diffraction peak of the IL-RGO sample in FIG. 4c and its low intensity may be because different interlayer spaces were obtained after ionic liquid functionalization, thus suggesting that exfoliation of layered IL-RGO was obtained. FIG. 4d shows the XRD peaks of TiO$_2$. The relatively noisy XRD spectrum is likely due to the presence of IL-RGO in the sample. Both anatase and rutile phases are present in the IL-RGO/TiO$_2$ sample. The anatase TiO$_2$ accounts for 73% while rutile phase TiO$_2$ contributes to 27%. The fractional content determined are very similar to the ratio of anatase and rutile of Degussa P25, which is the TiO$_2$ precursor in this work.

Figure 5:
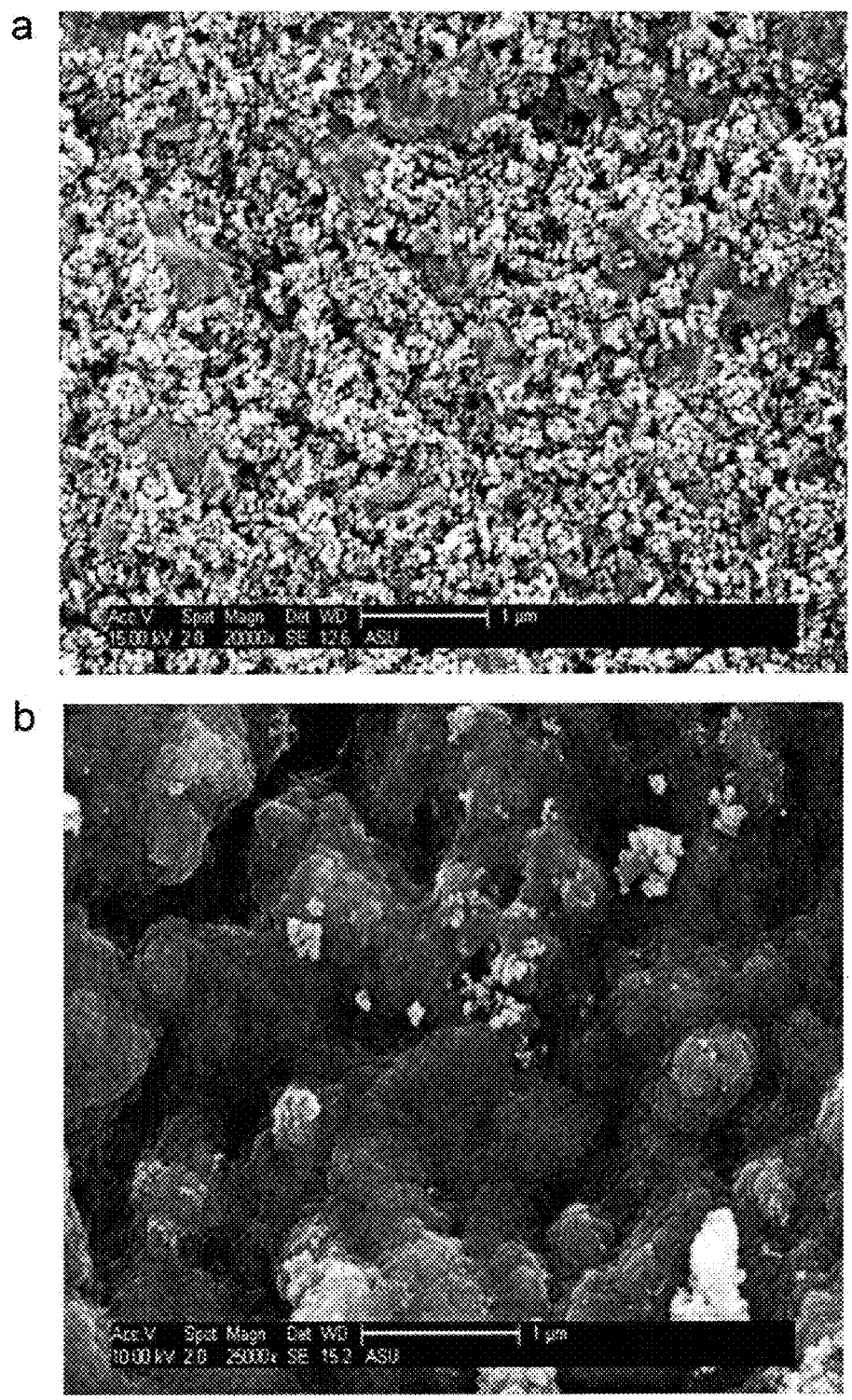
FIG. 5 shows SEM images of (a) IL-RGO/$TiO_2$ and (b) RGO/$TiO_2$.

The scanning electron micrographs (SEM) of IL-RGO/TiO$_2$ and RGO/TiO$_2$ are shown in FIG. 5. The separated RGO flakes can be clearly seen in the IL-RGO/TiO$_2$ sample in FIG. 5a. However, without the functionalized IL as in FIG. 5b, the RGO particles are much larger in the RGO/TiO$_2$ sample and aggregate together. A few TiO$_2$ nanoparticles exist above the RGO aggregates, but the majority of the $TiO_2$ nanoparticles are covered by the RGO. Due to the thickness of the multi-layer RGO, the $TiO_2$ nanoparticles below the RGO cannot be clearly seen in the SEM image. When the IL-RGO/$TiO_2$ solution and the RGO-$TiO_2$ solution were centrifuged, the IL-RGO and $TiO_2$ were well mixed while the RGO and $TiO_2$ were separated. The SEM images reveal that better separation of the graphite layers can be obtained with the IL-RGO material. The presence of the functionalized ionic liquid enhances the solubility of functionalized reduced graphite oxide in water. Thus, a well-mixed IL-RGO and $TiO_2$ could be obtained in solution.

Photocatalytic Reduction of $CO_2$ Over IL-RGO/$TiO_2$ and Bare P25 with $H_2O$ Vapor The experiments on the photoreduction of $CO_2$ were carried out using a Nicolet 6700 Fourier transform infrared (FTIR) spectrometer equipped with a Praying Mantis diffuse reflectance accessory (Harrick Sci. Corp., Model DRP-M-07) and a 316 stainless steel high temperature reaction chamber (Harrick Sci. Corp., Model HVC-DRP-4), a mercury cadmium telluride (MCT) detector and a KBr beam splitter. The chamber dome has two KBr windows and a quartz window. The quartz window was used for visual observation while the KBr windows were used to permit entry and exit of the infrared beam.

The IL-RGO/$TiO_2$ or pristine Degussa P25 powders were placed in the sample compartment of the reaction chamber, and the dome was mounted and sealed with an O-ring. The reaction chamber has an inlet for introducing gas to the sample and an outlet for gas exhaust. The chamber was purged with $N_2$ before introducing the $CO_2$ and $H_2O$ vapor reactant gases. The $H_2O$ vapor was obtained by flowing $N_2$ through an impinger containing distilled water. $CO_2$ mixed with humidified $N_2$ was introduced to the reaction chamber. Mass flow controllers (Omega Engineering, Inc.) were used to control the flow of $CO_2$ and $N_2$. The inlet mixing ratio of $CO_2$ is 10% by volume. An IR spectrum was obtained after the $CO_2$/humidified $N_2$ mixture flowed over the photocatalyst, in order to check that $CO_2$ and $H_2O$ vapor were absorbed to the surface of the catalyst. The inlet and outlet of the chamber were sealed, and subsequent spectra were taken in a batch mode of operation.

A series of background experiments were conducted in order to characterize the system and to ensure the absence of product formation, even in the presence of the catalytic surface. The sample with $CO_2$ and humidified $N_2$ was kept in the dark for 30 minutes. IR spectra were obtained during the 30 minutes dark period to examine whether products formed in the absence of light. In addition, a background experiment with the catalyst and humidified $N_2$ but without $CO_2$ was performed under UV-Visible light irradiation in order to determine whether there was product formation in the absence of $CO_2$. After performing the background experiments, the catalyst (IL-RGO/$TiO_2$ or P25) was placed in the chamber with $CO_2$ and humidified $N_2$. UV-Visible light, produced from a deuterium-halogen light source (Ocean Optics DH-2000-BAL, wavelength=210-1500 nm), was used to activate the catalyst. An optical fiber cable was used to introduce the light to the sample surface through the quartz window of the chamber. Several IR spectra at different irradiation times were acquired over a total irradiation time of 60 minutes. Each spectrum was acquired using 4 $cm^{-1}$ resolution and 32 scans.

To attempt to quantify the amount of product formed, standard samples of product (diluted by $N_2$) were admitted to the DRIFTS reaction cell to generate a calibration curve. The gas was allowed to equilibrate with the surface, a spectrum was obtained, and the surface was subsequently purged with $N_2$ in between each admission of product. Spectra were acquired during the $N_2$ purge to ensure that the product was completely desorbed from the surface and removed from the chamber. A surface adsorbed product calibration curve was generated and used to attempt to quantify the amount of product formed during the $CO_2$ photoreduction experiment over IL-RGO/$TiO_2$.

The $CO_2$ photoreduction using IL-RGO/$TiO_2$ catalyst in the presence of $H_2O$ vapor was performed twice using fresh and regenerated catalyst samples. Initially, fresh IL-RGO/$TiO_2$ was used for $CO_2$ photoreduction. After 30 minute UV-Visible irradiation, the sample was regenerated by cleaning the catalyst surface using pure $N_2$. IR spectra of the catalytic surface were obtained to ensure that the reactants ($CO_2$ and $H_2O$ vapor), and the $CH_4$ product formed in the previous run were completely dissociated from the catalyst surface and removed from the reaction chamber. Then, the reactants with the same concentrations were admitted to the reaction chamber and the photoreduction experiment was performed again.

In the background experiments, no new peaks were observed in the IR spectra of IL-RGO/$TiO_2$ with $CO_2$ and humidified $N_2$ in the dark over 30 minutes. When IL-RGO/$TiO_2$ and humidified $N_2$ (in the absence of $CO_2$) were irradiated for 30 minutes using UV-Vis light, no new peaks were detected in the IR spectra. Experiments were also performed for bare P25 with $CO_2$ and humidified $N_2$. Even after 60 minutes of UV-Vis irradiation, no new peak formation was detected in the IR spectra.

Figure 6:
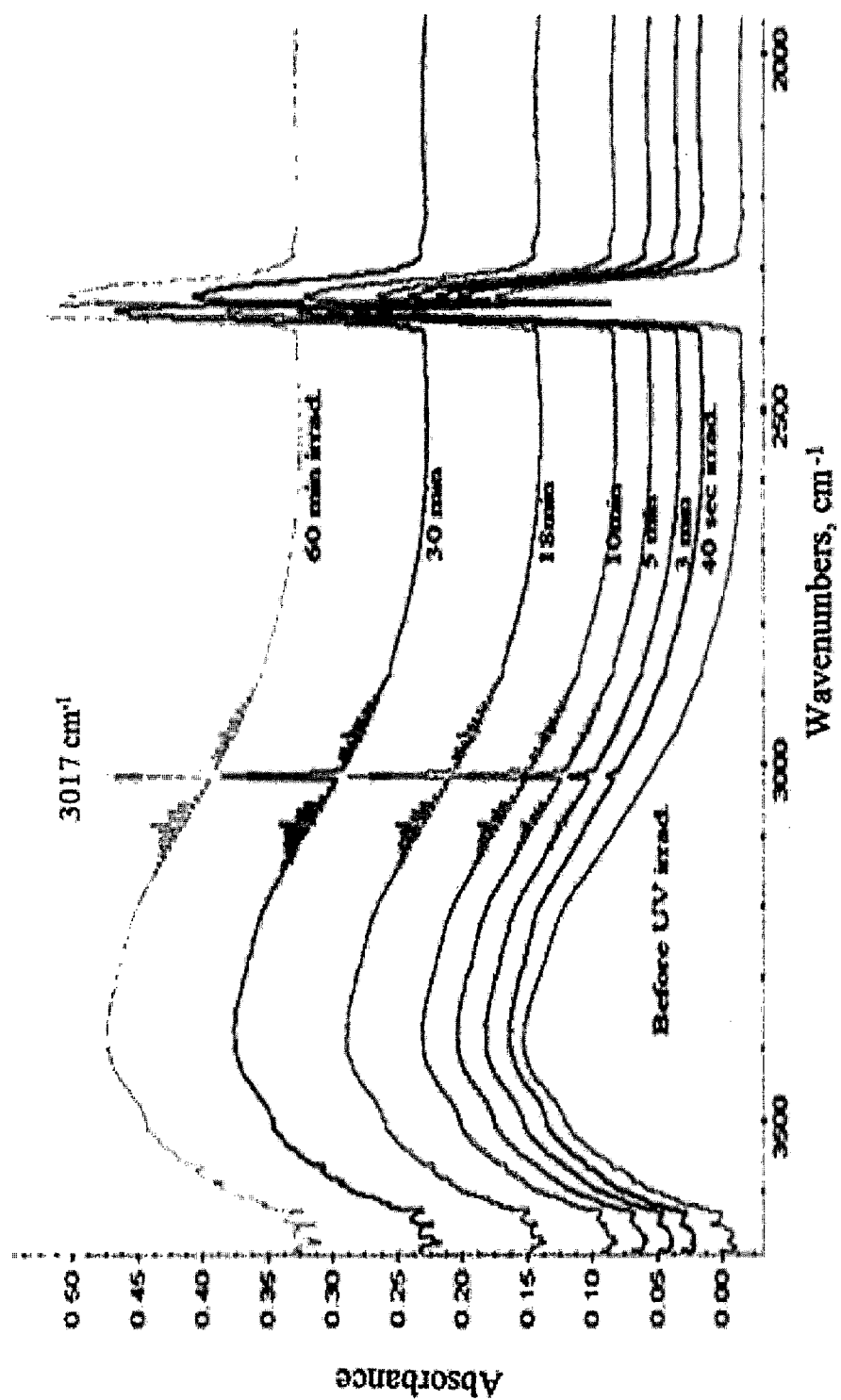
FIG. 6 shows the IR spectra of IL-RGO/$TiO_2$ surface with $CO_2$ and $H_2O$ vapor before and after UV-Visible light irradiation. The IR spectrum of IL-RGO/$TiO_2$ was used as a background. The IR spectra were offset for clarification.
Figure 7:
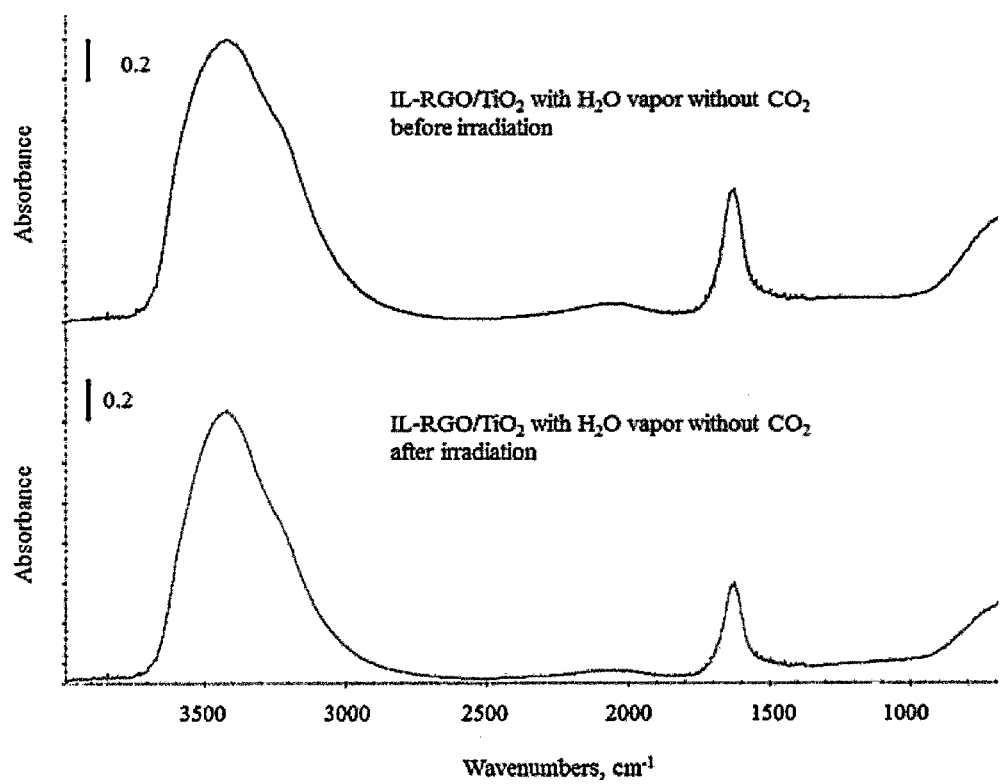
FIG. 7 shows the IR spectra of IL-RGO/$TiO_2$ with $H_2O$ but without $CO_2$ before and after 30 minute UV-Visible irradiation.

The IL-RGO/$TiO_2$ composite material was applied to the photoreduction of $CO_2$ in the presence of $H_2O$ vapor. IR spectra of the IL-RGO/$TiO_2$ surface before and after UV-Visible irradiation were obtained and are shown in FIG. 6. After only 40 seconds of irradiation, new IR features started to appear in the spectrum. In going from 40 seconds to 60 minutes of irradiation, a new peak at 3017 $cm^{-1}$ continued to grow in intensity. The new peak was initially identified by comparison to the literature as being characteristic of $CH_4$. In addition, a standard IR spectrum of pure $CH_4$ over IL-RGO/$TiO_2$ was created in-house and compared with the product's IR spectrum. A comparison confirmed that $CH_4$ was indeed the product from reduction of the $CO_2$ in the presence of water vapor. The background experiments of IL-RGO/$TiO_2$ with $H_2O$ vapor but without $CO_2$ showed that no peak formed after 30 minutes of UV-Vis irradiation as evidenced by FIG. 7, thus confirming that $CH_4$ was indeed formed from $CO_2$ reduction in the presence of water vapor rather than from other carbon sources (i.e. RGO or the attached ionic liquid).

Figure 8:
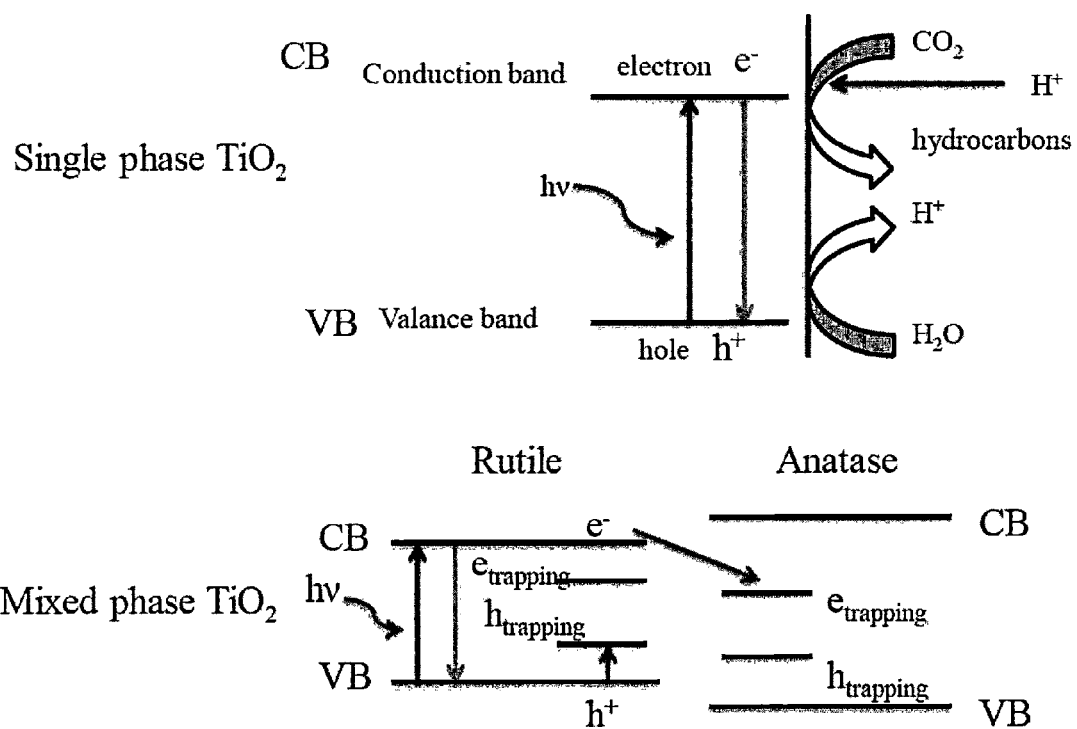
FIG. 8 shows energy level diagrams for single phase and mixed phase $TiO_2$.
Figure 9:
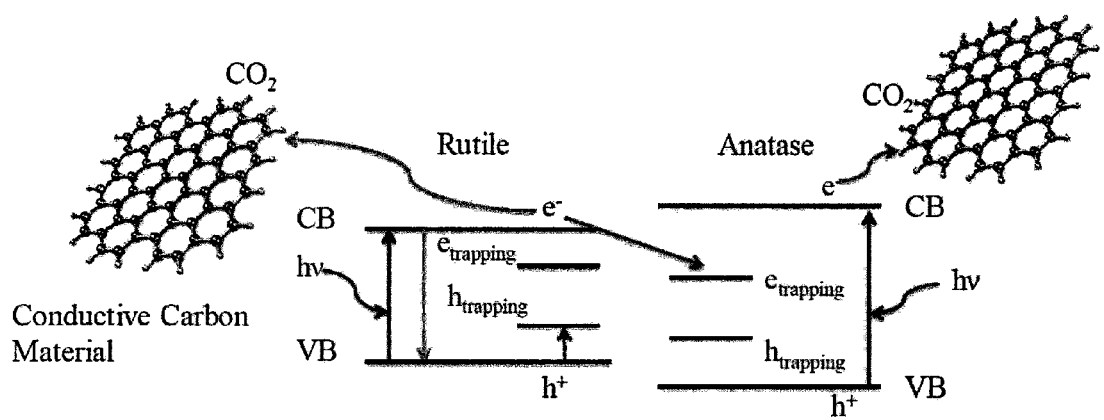
FIG. 9 shows and energy level diagram for the one embodiment of the IL-RGO/$TiO_2$ structure.

The major challenge in $CO_2$ photoreduction is that the recombination of electron and hole generated from $TiO_2$ is very fast. Thus, there is a significant decrease in the photocatalytic efficiency of $TiO_2$. P25, which is the mixed phases of $TiO_2$ with approximately 75% anatase and approximately 25% rutile, is expected to have better electron and hole separation than a single phase of $TiO_2$ due to the different positions of the conduction and valence bands of the anatase and rutile phases such as is illustrated in FIG. 8.

Electron paramagnetic resonance (EPR) studies by Gray and co-workers indicated that photogenerated electrons actually migrated from rutile to lower energy anatase trapping sites, consequently enhancing electron-hole separation. See, for example: Hurum, D. C.; Agrios, A. G.; Gray, K. A.; Rajh, T.; Thurnauer, M. C., Explaining the enhanced photocatalytic activity of Degussa P25 mixed-phase $TiO_2$ using EPR. Journal of Physical Chemistry B 2003, 107, 4545-4549; Hurum, D. C.; Gray, K. A.; Rajh, T.; Thurnauer, M. C., Recombination pathways in the Degussa P25 formulation of $TiO_2$: Surface versus lattice mechanisms. Journal of Physical Chemistry B 2005, 109, 977-980; and Hurum, D. C.; Agrios, A. G.; Crist, S. E.; Gray, K. A.; Rajh, T.; Thurnauer, M. C., Probing reaction mechanisms in mixed phase $TiO_2$ by EPR. Journal of Electron Spectroscopy and Related Phenomena 2006, 150, 155-163.

However, when P25 was used in the $CO_2$ photoreduction experiments, no product was observed under the DRIFTS experimental conditions. Therefore, the commercial P25 was still not effective enough for the photoreduction of $CO_2$ with $H_2O$ vapor. Nevertheless, it was found that the presence of IL-RGO significantly enhances the photoactivity of P25 which is likely due to the improved electron-hole separation via electron transport from the $TiO_2$ to the IL-RGO.

The production of CO is frequently reported in the literature as the major product for $CO_2$ photoreduction studies using $TiO_2$-based nanoparticles. The IR feature of CO is expected to appear in the 2000-2270 $cm^{-1}$ frequency range. Notably, the lack of CO features in FIG. 6 suggests that there is insignificant production of CO, and $CH_4$ is the only product of $CO_2$ photoreduction in the presence of water vapor over IL-RGO/$TiO_2$.

Additionally, in the literature, there are different proposed mechanisms for $CH_4$ formation in $CO_2$ photoreduction using $TiO_2$-based photocatalysts. The selectivity of the products, for example CO or $CH_4$, may be due to differences in the numbers of electrons that are produced by the catalyst and separated from the holes. As reported for photochemical reduction of $CO_2$, the reaction mechanism for CO production requires four electrons, while eight electrons are needed for $CH_4$ production. The selective formation of $CH_4$ that is reported herein suggests that more electrons are available from the IL-RGO/$TiO_2$ material as compared to the catalysts used in published studies that have CO as the major product of $CO_2$ photoreduction. This further confirms that the presence of IL-RGO helps to separate electron and hole pairs. The selective production of $CH_4$ is very valuable in the application of the catalyst in $CO_2$ photoreduction because CO, as a synthesis gas, cannot be used as a fuel directly whereas $CH_4$ is an energy-rich fuel.

Figure 10:
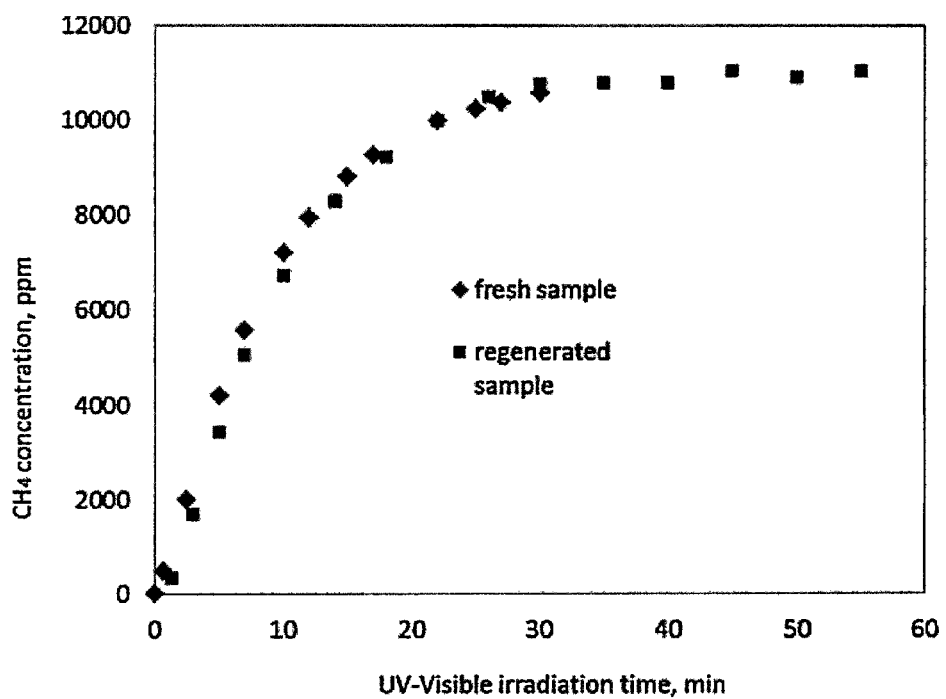
FIG. 10 shows the concentration of methane over IL-RGO/$TiO_2$ and regenerated sample by cleaning the surface using $N_2$ at different UV-Visible irradiation times.

In FIG. 10, the concentration of $CH_4$ formed at different UV-Visible irradiation times by fresh IL-RGO/$TiO_2$ catalyst and regenerated IL-RGO/$TiO_2$ catalyst are shown. The results show that the regenerated sample can produce an almost identical amount of $CH_4$ at the same irradiation times. These preliminary results suggest that the IL-RGO/$TiO_2$ catalyst can be regenerated and effectively reused in $CO_2$ photoreduction. This result is significant in that it signifies the real-world application of this material in $CO_2$ photoreduction. The $CH_4$ production rate of 279 µmol/g catalyst-hr over a 55 minute period was calculated. The $CH_4$ production rate is about 20-30 times higher as compared to the highest $CH_4$ production rate using other modified $TiO_2$ structure reported in the literature.

Although the present invention has been described in detail with reference to certain embodiments, one skilled in the art will appreciate that the present invention can be practiced by other than the described embodiments, which have been presented for purposes of illustration and not of limitation. Therefore, the scope of the invention should not be limited to the description of the embodiments contained herein. For example, it is contemplated that another application for this material or other materials made by similar processes may exist in Field Effect Transistors.

What is claimed is:

1. A photocatalytic nanocomposite comprising:
    a reduced graphite oxide;
    a photocatalytic metal oxide in nanoparticle form; and
    an ionic moiety attached to the reduced graphite oxide;
    wherein the photocatalytic metal oxide in nanoparticle form is dispersed in the reduced graphite oxide.

2. The photocatalytic nanocomposite of claim 1, wherein the ionic moiety comprises $R_1R_2R_3$ and wherein $R_1$ is NH, $R_2$ is alkylene, and $R_3$ is a cationic group.

3. The photocatalytic nanocomposite of claim 2, wherein $R_2$ is $C_1$ to $C_5$ alkylene, and $R_3$ is an imidazole ring protonated or substituted at a nitrogen atom.

4. The photocatalytic nanocomposite of claim 3, wherein $R_2$ is propylene, and $R_3$ is an alkyl-substituted imidazole ring.

5. The photocatalytic nanocomposite of claim 1, wherein the reduced graphite oxide is an ionic liquid functionalized reduced graphite oxide formed by attaching a $NH_2$-terminated ionic liquid to the reduced graphite oxide.

6. The photocatalytic nanocomposite of claim 1, wherein the photocatalytic metal oxide is $TiO_2$.

7. The photocatalytic nanocomposite of claim 6, wherein the $TiO_2$ is in the form of rutile and anatase.

8. The photocatalytic nanocomposite of claim 1, wherein the reduced graphite oxide is a powder.

9. A method of making a photocatalytic nanocomposite comprising:
    oxidizing graphite to form a reduced graphite oxide;
    attaching an ionic moiety to the reduced graphite oxide; and
    mixing the reduced graphite oxide with a photocatalytic metal oxide in nanoparticle form to form the photocatalytic nanocomposite.

10. The method of claim 9, further comprising the step of functionalizing the reduced graphite oxide with a $NH_2$-terminated ionic liquid to form an ionic liquid functionalized reduced graphite oxide before the step of mixing.

11. The method of claim 10, wherein the $NH_2$-terminated ionic liquid is an imidazole.

12. The method of claim 10, wherein the $NH_2$-terminated ionic liquid is a 1-butyl-3-methylimidazolium-based ionic liquid.

13. The method of claim 10, wherein the $NH_2$-terminated ionic liquid is a 1-butyl-3-methylimidazolium chloride.

14. A method of $CO_2$ photoreduction comprising:
    contacting reactants of $CO_2$ and $H_2O$ over a photocatalytic nanocomposite according to claim 1;
    reacting the $CO_2$ and $H_2O$ over the photocatalytic nanocomposite to produce products including $CH_4$.

15. The method of claim 14, wherein the products are substantially free of CO gas.

16. The method of claim 14, wherein the $CH_4$ has a production rate in excess of 10 µmol/g catalyst-hr.

17. The method of claim 14, wherein the $CH_4$ has a production rate in excess of 250 µmol/g catalyst-hr.

18. The method of claim 9, wherein the photocatalytic metal oxide is $TiO_2$.

* * * * *

UNITED STATES PATENT AND TRADEMARK OFFICE
CERTIFICATE OF CORRECTION

| | | |
|---|---|---|
| PATENT NO. | : 9,545,625 B2 | Page 1 of 1 |
| APPLICATION NO. | : 14/076764 | |
| DATED | : January 17, 2017 | |
| INVENTOR(S) | : Jean Andino et al. | |

It is certified that error appears in the above-identified patent and that said Letters Patent is hereby corrected as shown below:

In the Specification

Column 4, Line 7:
Replace "TIO2" with --TiO2--

Column 5, Line 44:
Replace "1 L" with --IL--

Column 7, Line 56:
Replace "IL-RGO/TIO2" with --IL-RGO/TiO2--

Signed and Sealed this
Sixth Day of June, 2017

Michelle K. Lee
*Director of the United States Patent and Trademark Office*